(12) United States Patent
Sato et al.

(10) Patent No.: US 8,784,972 B2
(45) Date of Patent: Jul. 22, 2014

(54) COMPOSITE SHEET

(75) Inventors: Kenichi Sato, Tochigi (JP); Kenji Ando, Tochigi (JP); Takuaki Harada, Tochigi (JP); Yasuhiro Nakano, Tochigi (JP)

(73) Assignee: Kao Corporation, Tokyo (JP)

( * ) Notice: Subject to any disclaimer, the term of this patent is extended or adjusted under 35 U.S.C. 154(b) by 462 days.

(21) Appl. No.: 12/679,388

(22) PCT Filed: Oct. 30, 2008

(86) PCT No.: PCT/JP2008/069738
§ 371 (c)(1),
(2), (4) Date: May 7, 2010

(87) PCT Pub. No.: WO2009/069424
PCT Pub. Date: Jun. 4, 2009

(65) Prior Publication Data
US 2010/0209664 A1    Aug. 19, 2010

(30) Foreign Application Priority Data

Nov. 26, 2007   (JP) .................................. 2007-305014

(51) Int. Cl.
| | | |
|---|---|---|
| *B32B 3/10* | (2006.01) | |
| *B32B 3/28* | (2006.01) | |
| *B32B 5/26* | (2006.01) | |
| *B32B 38/06* | (2006.01) | |
| *B32B 7/02* | (2006.01) | |

(52) U.S. Cl.
CPC ... *B32B 3/28* (2013.01); *B32B 5/26* (2013.01); *B32B 38/06* (2013.01); *B32B 7/02* (2013.01)
USPC ........... 428/166; 428/170; 428/132; 428/156; 428/172; 428/178; 428/180

(58) Field of Classification Search
CPC ............ B32B 3/28; B32B 5/26; B32B 38/06; B32B 7/02
USPC .......... 428/170, 132, 156, 166, 172, 178, 180
See application file for complete search history.

(56) References Cited

U.S. PATENT DOCUMENTS

| | | |
|---|---|---|
| 2,115,577 A | 4/1938 | Goldman |
| 2,974,716 A | 3/1961 | Fourness |

(Continued)

FOREIGN PATENT DOCUMENTS

| | | |
|---|---|---|
| CN | 1349789 A | 5/2002 |
| CN | 1500828 A | 6/2004 |

(Continued)

OTHER PUBLICATIONS

Office Action mailed Jun. 8, 2010 for Japanese Application No. 2007-276679.

(Continued)

*Primary Examiner* — William P Watkins, III
(74) *Attorney, Agent, or Firm* — Birch, Stewart, Kolasch & Birch, LLP (57) ABSTRACT

Disclosed is a composite sheet 1 composed of a substantially flat lower fibrous sheet 3 and an upper fibrous sheet 2 bonded to the lower fibrous sheet 3. The upper fibrous sheet 2 is three-dimensionally textured with a number of projections 5 and a number of depression 6 each of which is located between every adjacent two of the projections 5. The projections 5 and the depressions 6 alternate in both a first direction of the composite sheet 1 and a second direction perpendicular to the first direction. Each projection 5 has a pair of opposing first walls 51 parallel to the first direction and a pair of opposing second walls 52 parallel to the second direction. The basis weight of the first walls 51 is different from that of the second walls 52.

8 Claims, 5 Drawing Sheets

(56) References Cited

U.S. PATENT DOCUMENTS

| | | | |
|---|---|---|---|
| 3,193,434 A | | 7/1965 | Weiss |
| 4,323,088 A | | 4/1982 | Aziz |
| 4,614,632 A | | 9/1986 | Kezuka et al. |
| 4,735,738 A | | 4/1988 | Willman |
| 5,558,923 A | | 9/1996 | Vesamaa |
| 5,705,249 A | | 1/1998 | Takai et al. |
| 5,932,316 A | | 8/1999 | Cree et al. |
| 6,013,063 A | | 1/2000 | Roe et al. |
| 6,153,037 A | | 11/2000 | Kim et al. |
| 6,311,754 B1 | | 11/2001 | Marschke |
| 6,409,857 B2 | | 6/2002 | Pallas et al. |
| 6,586,076 B1 * | | 7/2003 | Mizutani et al. ............ 428/173 |
| 7,410,683 B2 * | | 8/2008 | Curro et al. ............... 428/133 |
| 7,468,114 B2 | | 12/2008 | Sato et al. |
| 7,851,047 B2 | | 12/2010 | Sato et al. |
| 2004/0140047 A1 | | 7/2004 | Sato et al. |
| 2007/0020412 A1 | | 1/2007 | Kumamoto et al. |
| 2008/0108962 A1 | | 5/2008 | Furuta et al. |
| 2011/0042011 A1 | | 2/2011 | Sato et al. |

FOREIGN PATENT DOCUMENTS

| | | |
|---|---|---|
| CN | 101035493 A | 9/2007 |
| EP | 0341993 A1 | 11/1989 |
| EP | 1184016 A2 | 3/2002 |
| EP | 1190690 A2 | 3/2002 |
| EP | 1226801 A2 | 7/2002 |
| EP | 1 803 429 A1 | 7/2007 |
| GB | 2277480 A | 11/1994 |
| JP | 35-16985 Y | 7/1960 |
| JP | 49-46062 U | 4/1974 |
| JP | 2-18038 A | 1/1990 |
| JP | 3-11198 A | 5/1991 |
| JP | 5-59855 A | 11/1994 |
| JP | 5-304203 A | 11/1994 |
| JP | 10-245757 A | 9/1998 |
| JP | 11-504685 A | 4/1999 |
| JP | 11-286863 A | 10/1999 |
| JP | 2000-197930 A | 7/2000 |
| JP | 2001-20168 A | 1/2001 |
| JP | 2002-185830 A | 6/2002 |
| JP | 2002-527642 A | 8/2002 |
| JP | 2003-33966 A | 2/2003 |
| JP | 2003-94125 A | 4/2003 |
| JP | 2003-521947 A | 7/2003 |
| JP | 2003-521969 A | 7/2003 |
| JP | 2004-174234 A | 6/2004 |
| JP | 2005-58248 A | 3/2005 |
| JP | 2005-111908 A | 4/2005 |
| JP | 2005-319730 A | 11/2005 |
| JP | 2006-115974 A | 5/2006 |
| JP | 2007-130817 A | 5/2007 |
| JP | 2007-175093 A | 7/2007 |
| JP | 2008-229033 A | 10/2008 |
| WO | WO 99/42068 A1 | 8/1999 |
| WO | WO 00/23024 A1 | 4/2000 |
| WO | WO 01/06874 A1 | 2/2001 |

OTHER PUBLICATIONS

International Preliminary Report on Patentability, International Preliminary Report on Patentability and Written Opinion of the International Searching Authority dated Jun. 17, 2010 for International Application No. PCT/JP2008/069738 (Forms PCT/IB/338, PCT/IB/373 and PCT/ISA/237).

Extended European Search Report for European Application No. 0885439.0 dated Jun. 6, 2012.

Notification of the First Office Action for corresponding Chinese Patent Application No. 200880113640.6, dated Jun. 20, 2012.

European Search Report for Application No. EP-03026153, dated Mar. 3, 2004.

Extended European Search Report for Application No. EP-06012863, dated Jul. 22, 2009.

Notice of Rejection in Japanese Application No. 2003-351594, May 15, 2007.

Notice of Rejection in Japanese Application No. 2003-351691, Aug. 28, 2007.

Office Action (final) for U.S. Appl. No. 10/704,908, dated Sep. 12, 2006.

Office Action (final) for U.S. Appl. No. 10/704,908, dated Sep. 18, 2007.

Office Action (non-final) for U.S. Appl. No. 10/704,908, dated Jan. 11, 2008.

Office Action (non-final) for U.S. Appl. No. 10/704,908, dated Mar. 8, 2006.

Office Action (non-final) for U.S. Appl. No. 10/704,908, dated Mar. 8, 2007.

Office Action (non-final) for U.S. Appl. No. 12,292,373, dated Nov. 2, 2009.

Office Action(Quayle) for U.S. Appl. No. 12/292,373, dated May 20, 2010.

* cited by examiner

COMPOSITE SHEET

TECHNICAL FIELD

The present invention relates to a composite sheet having projections and depressions and a process of producing the same.

BACKGROUND ART

Applicant previously proposed a topsheet for use on the skin facing side of an absorbent article (see Patent Document 1). The topsheet is composed of an upper layer and a lower layer both formed of a substantially inextensible sheet which are partially bonded to each other at a number of joints. The upper layer project outward toward the skin of a wearer in other than the areas of the joints to form a number of projections. The topsheet exhibits excellent leak-proof against liquid, especially a highly viscous liquid, such as loose stool or menstrual blood, and high capability of hiding absorbed liquid.

Nevertheless, the demand has ever been increasing for the improvement of performance of absorbent articles.

Patent Document 1 US 200410140047A1

The present invention provides a composite sheet comprising a substantially flat lower fibrous sheet and an upper fibrous sheet bonded to the lower fibrous sheet, the upper fibrous sheet being three-dimensionally textured with a number of projections and a number of depression each of which is located between every adjacent two of the projections, the projections and the depressions alternating in a first direction of the composite sheet and in a second direction perpendicular to the first direction, the projections each having a pair of opposing first walls parallel to the first direction, a pair of opposing second walls parallel to the second direction, and a top plane connected to the upper edge of each first wall and the upper edge of each second wall, and the basis weight of each first wall being different from that of each second wall.

The present invention also provides a process of producing the composite sheet, the process comprising the steps of:

providing a first roller having projections and depressions on the peripheral surface thereof and rotating in one direction and a second roller having projections and depressions mating with the depressions and the projections of the first roller on the peripheral surface thereof and rotating in the opposite direction to at substantially the same rotating speed as the first roller, feeding an upper fibrous sheet into an engaged portion between the rollers at a speed higher than a peripheral speed of the rollers, three-dimensionally texturing the upper fibrous sheet by the engagement of the rollers while holding the upper fibrous sheet to the periphery of the first roller by suction, superposing a lower fibrous sheet on the textured upper fibrous sheet while holding the upper fibrous sheet to the periphery of the first roller by suction, and bonding the two fibrous sheets at their parts located on the top faces of the projections of the first roller.

BRIEF DESCRIPTION OF DRAWINGS

[FIG. 1]

[FIG. 2]

[FIG. 3] FIG. 3(a) and FIG. 3(b) each schematically illustrate a cross-sectional structure of a projection of the composite sheet shown in FIG. 1.

[FIG. 5]

[FIG. 6]

[FIG. 8]

DETAILED DESCRIPTION OF THE INVENTION

Figure 1:
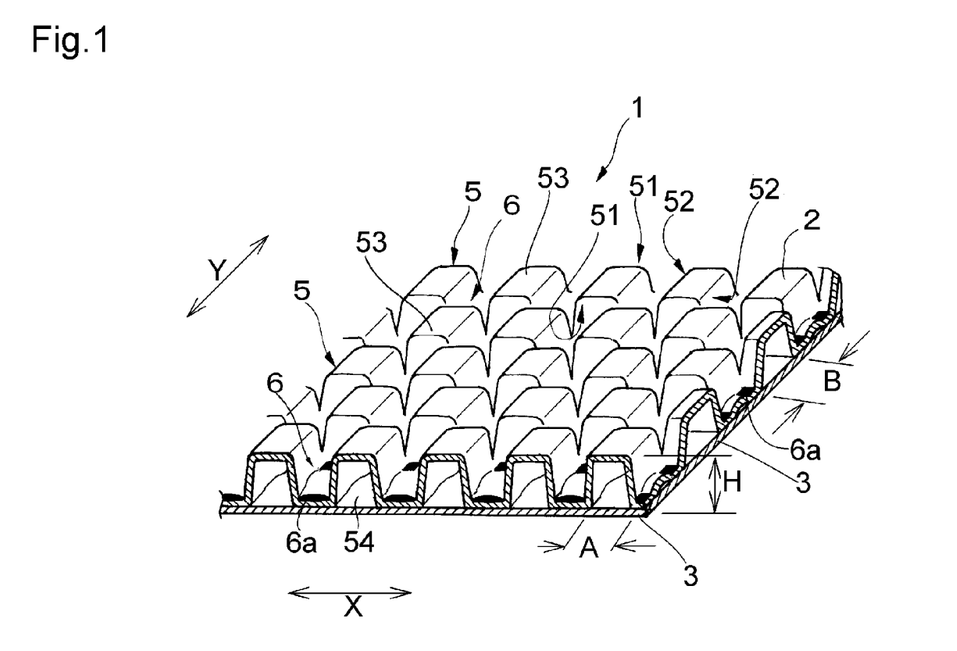
FIG. 1 is a perspective representing an embodiment of the composite sheet according to the present invention, with part cut away.

The present invention will be described based on its preferred embodiments with reference to the accompanying drawing. FIG. 1 is an enlarged fragmentary view of an embodiment of the composite sheet according to the invention. The composite sheet 1 shown in FIG. 1 is composed of an upper fibrous sheet 2 and the lower fibrous sheet 3 bonded together. The composite sheet 1 has a number of projections 5 and a number of depressions 6 each of which is located between projections 5. The projections 5 are formed by three-dimensionally texturing the upper fibrous sheet and joining it partially to the lower fibrous sheet 3 which is substantially flat at a number of joints 6a. The upper layer 2 protrudes to the skin of a wearer to form the projections 5. The projections 5 are hollow. Each one of the depressions 6 is between adjacent two of the projections 5.

The projections 5 and the depressions 6 alternate in direction X indicated in FIG. 1. The projections 5 and the depressions 6 also alternate in direction Y that is perpendicular to direction X. In a plan view of the composite sheet 1, taken from the side of the upper fibrous sheet, the projections 5 and the depressions 6 are arranged in a staggered pattern (see FIG. 2, infra). With the projections 5 and the depressions 6 being so arranged, the composite sheet 1, when used as, for example, a topsheet of an absorbent article, provides a highly leakproof absorbent article. More specifically, the following effects are produced when the composite sheet 1 is used, for example, as a topsheet of a disposable diaper especially a diaper designed for few months old babies who pass loose stools, highly viscous body waste. In general, loose stool, being highly viscous, hardly passes through a topsheet rapidly but tends to stay and flow laterally on the topsheet. The composite sheet 1 of the present embodiment traps loose stool in the closed depressions 6 surrounded by the projections 5 and is therefore less likely to allow the loose stool to flow laterally. Being so trapped, loose stool is then forced to migrate downward (i.e., into the absorbent member). Leakage of loose stool is thus prevented. In addition, the projections 5, being hollow, produce an effect of hiding the color of soft stool absorbed by the absorbent member. The same effects are enjoyed when the composite sheet 1 of the present embodiment is applied as a topsheet of a sanitary napkin for absorbing menstrual blood, which is also a highly viscous bodily waste.

Each projection 5 has a pair of opposing first walls 51 parallel to direction X indicated in FIG. 1 and a pair of opposing second walls 52 parallel to direction Y perpendicular to direction X. The projection 5 has a top plane 53 connected to the upper edge of each first wall 51 and the upper edge of each second wall 52. The projection 5 is a flat rectangular prism or a flat truncated quadrangular pyramid, each with rounded edges. The projection has a bottom plane 54 that opposes the top plane 53. The first walls 51, the second walls 52, and the top plane 53 are formed of the upper fibrous sheet 2, and the bottom plane 54 is formed of the lower fibrous sheet 3.

Figure 2:
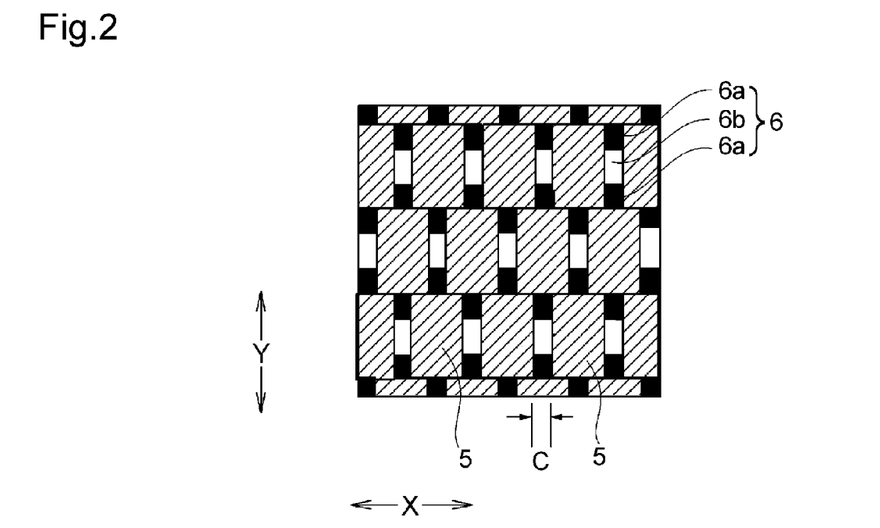
FIG. 2 is a plan of the composite sheet shown in FIG. 1, seen from the upper fibrous sheet side.

FIG. 2 is a plan of the composite sheet 1 of FIG. 1. As illustrated in FIG. 2, each depression 6 is composed of a bonded region 6a, a non-bonded region 6b, and a bonded region 6a arranged in that order in the direction perpendicular to a line of alternating projections 5 and depressions 6 (a line extending in direction X in FIG. 2), i.e., in direction Y. The non-bonded regions 6b are arranged on a straight line extending in direction X. As illustrated in FIG. 2, one projection 5 is surrounded by six bonded regions 6a. The six bonded regions 6a are formed corresponding to the six projections in the projections 17 of the first roller 11 shown in FIG. 5 infra, wherein the top area of the six projections are represented by mesh.

In the composite sheet 1 of the present embodiment, directions X and Y indicated in FIGS. 1 and 2 are coincide with the machine direction (MD) and the cross direction (CD), respectively, in the production of the composite sheet.

Figures 3A, 3B:
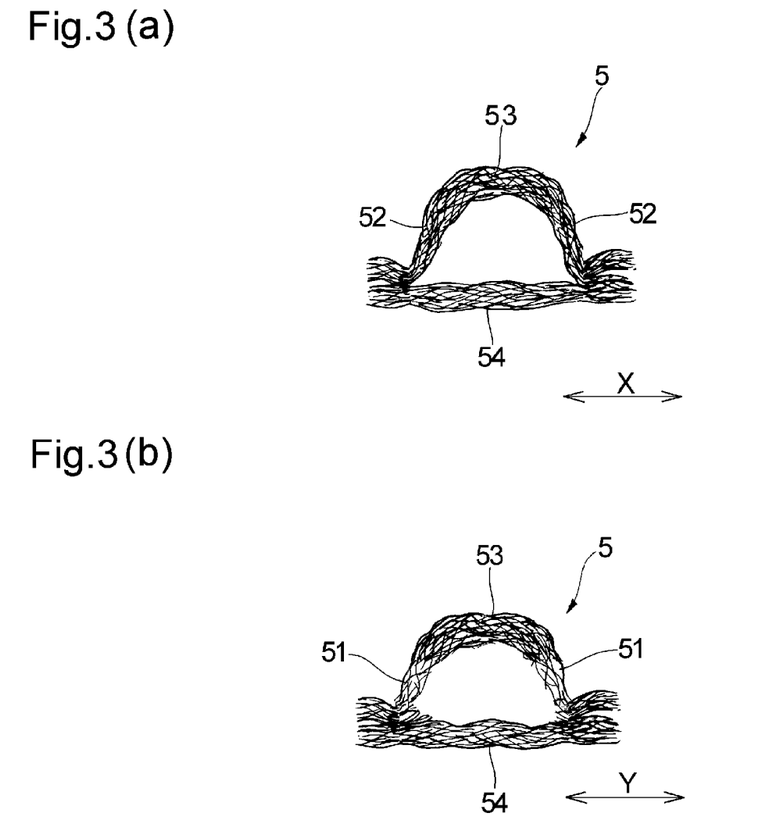

FIGS. 3(a) and 3(b) each schematically illustrate a cross-section of one of the projections 5 shown in FIGS. 1 and 2. FIG. 3(a) is taken parallel to direction X (MD) and shows the top plane 53, the bottom plane 54, and a pair of the second walls 52. FIG. 3(b) is taken parallel to direction Y (CD) and shows the top plane 53, the bottom plane 54, and a pair of the first walls 51. As is clear from the comparison between FIGS. 3(a) and 3(b), the projection 5 has its basis weight varied between the first walls 51 and the second walls 52. Specifically, the projection 5 has a smaller basis weight in the first walls 51 than in the second walls 52. Having different basis weights between the first walls 51 and the second walls 52, the composite sheet of the present embodiment has the following advantages. Where the composite sheet 1 is used as, for example, a topsheet of an absorbent article, a fluid wicks preferentially through the first wall 51 with a smaller basis weight. That is, the topsheet exhibits improved liquid permeability compared with conventional topsheets, like the one disclosed in Patent Document 1 supra. Where the composite sheet 1 is used as, for example, a topsheet of an absorbent article, the second walls 52 with a larger basis weight serve for improved cushioning properties, providing the composite sheet 1 with a good hand. Thus, the composite sheet 1 exhibits a good hand inclusive of good cushioning properties while securing liquid permeability.

The basis weight of each of the first wall 51 and the second wall 52 is calculated from the weight and the area of a piece cut out of the respective walls. A plurality of, preferably at least 10, pieces each of the first wall 51 and the second wall 52 are measured to give an average basis weight of the first wall 51 and that of the second wall 52, by which to judge whether or not the first wall 51 and the second wall 52 have different basis weights. Whether the first wall 51 and the second wall 52 have different basis weights may also be judged by other methods, for example, by counting the number of fibers under microscopic observation.

When the first walls 51 have an extremely small basis weight, a hole may be made in some of them. Such a hole is favorable to control liquid permeability through the projections 5 of the composite sheet 1 of the present embodiment. In the case where a hole is made through the first wall 51, the hole may be cut in either one or both of the opposing first walls 51.

When the composite sheet 1 of the present embodiment is used as, for example, a topsheet of an absorbent article, it is preferred that the individual projections have a height H (see FIG. 1) of 0.3 to 10 mm, more preferably 0.7 to 5 mm, a dimension A at the bottom in direction X (MD) of 1.5 to 30 mm, more preferably 2 to 5 mm, a dimension B at the bottom in direction Y (CD) of 1.5 to 30 mm, more preferably 2 to 10 mm, and a bottom area of 2.25 to 900 mm$^2$, more preferably 4 to 50 mm$^2$.

It is preferred that the individual depressions 6 have a length C (see FIG. 2) in direction Y (CD) of 0.1 to 20 mm, more preferably 0.5 to 5 mm, to prevent a lateral flow of highly viscous bodily waste and to provide a good feel and high cushioning properties.

The upper fibrous sheet 2 and the lower fibrous sheet 3 are formed of fibrous sheets of the same or different fibrous materials. These two sheets are substantially inextensible. By the use of such sheets, the composite sheet 1 having a relief pattern of desired size in substantial agreement with the mating projections and depressions formed on the first and second rollers (hereinafter described) can be obtained in a stable manner and with good reproducibility. The expression "substantially inextensible" as used herein is intended to mean that the sheets have an elongation limit of 105% or lower and undergo destruction or permanent deformation at an elongation exceeding that limit.

Any fibrous sheet can be used as long as it is substantially inextensible. Useful fibrous sheets include nonwoven fabric prepared by carding, spun bonded nonwoven fabric, melt blown nonwoven fabric, hydroentangled nonwoven fabric, and needle punched nonwoven fabric. Fibers constructing these nonwoven fabrics preferably have a fineness of 1 to 20 dtex, more preferably 1.5 to 4 dtex, to secure sufficient strength and improved feel of the composite sheet 1.

The basis weight of the upper fibrous sheet 2 is preferably 10 to 100 g/m$^2$, more preferably 10 to 30 g/m$^2$, and that of the lower fibrous sheet 3 is preferably 5 to 50 g/m$^2$, more preferably 10 to 30 g/m$^2$. The basis weight of the composite sheet 1 inclusive of the upper fibrous sheet 2 and the lower fibrous sheet 3 is preferably 15 to 150 g/m$^2$, more preferably 20 to 60 g/m$^2$.

When the composite sheet 1 is used as a topsheet of an absorbent article, it is preferably assembled into an absorbent article with its direction X (MD) indicated in FIG. 1 coincide with the longitudinal direction of the absorbent article while the direction Y (CD) coinciding with the transverse direction of the absorbent article. To put it another way, it is preferred that the first walls 51 of the projections 5 are parallel to the longitudinal direction of the absorbent article, and the second walls 52 are parallel to the transverse direction of the absorbent article. The composite sheet 1 so disposed makes a wearer feel its cushioning properties for the following reason. The second walls 52 with an increased basis weight intersect with the transverse direction of the absorbent article, which is advantageous to prevent deformation or collapse of the projections due to the compressive force imposed in the lateral direction of the absorbent article particularly in the crotch portion.

Figure 4:
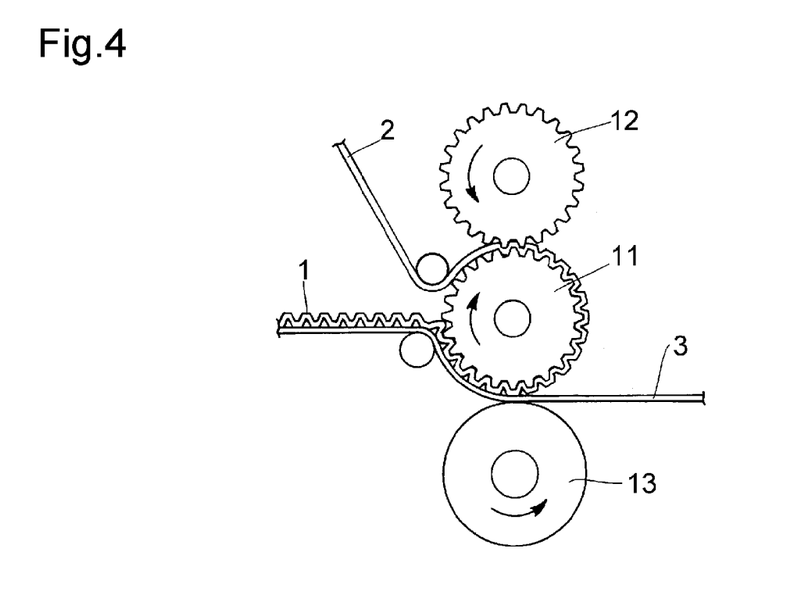
[FIG. 4] FIG. 4 schematically illustrates a process of producing the sheet of FIG. 1.
Figure 5:
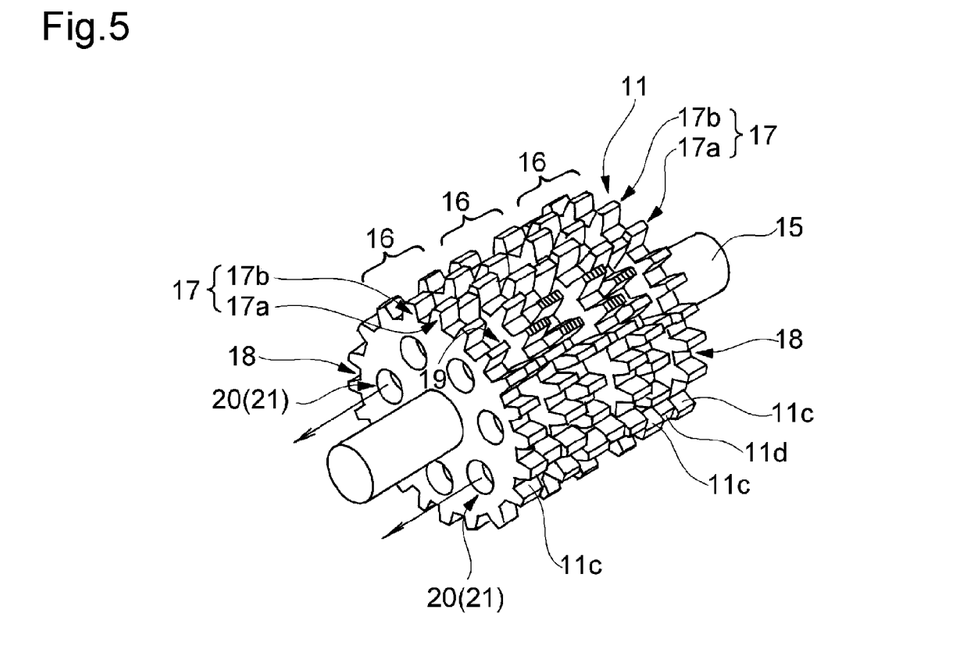
FIG. 5 is an enlarged partial view of the first roller in FIG. 4.
Figure 6:
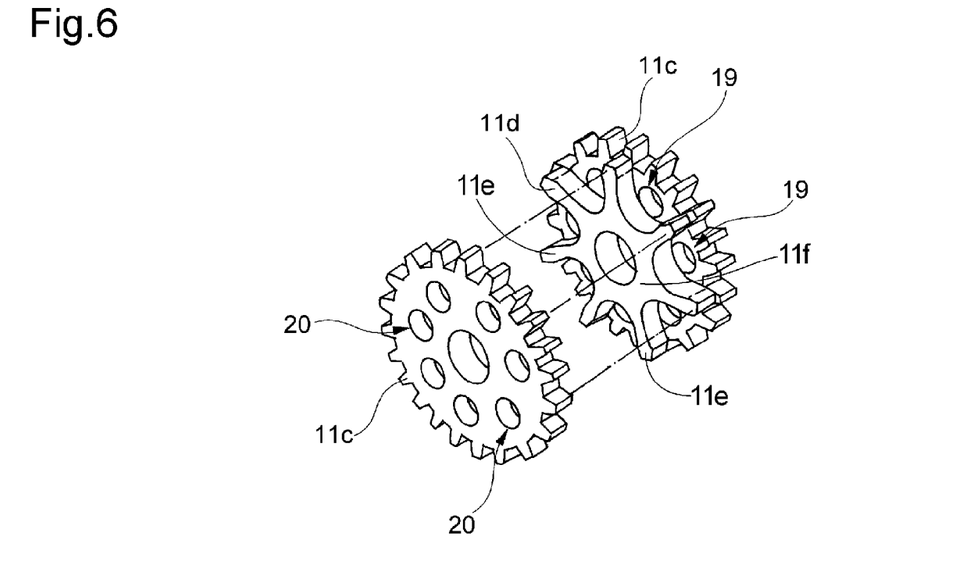
FIG. 6 is an exploded view of a part of the roller shown in FIG. 5.

A preferred process for producing the composite sheet 1 of the present embodiment will then be described by referring to FIGS. 4 through 6. As illustrated in FIG. 4, an upper fibrous sheet 2 and a lower fibrous sheet 3 are fed from their respective stock rolls (not shown). The unrolled upper fibrous sheet 2 is introduced into the engaged portion between a first roller 11 provided with projections and depressions on its periphery and a second roller 12 provided on its periphery with projections and depressions mating with the depressions and the projections of the first roller 11 to be textured three-dimensionally. As illustrated in FIG. 4, the first roller 11 rotates in one direction, and the second roller 12 rotates in the opposite direction to at substantially the same rotating speed as the first roller 11.

An enlarged view of part of the first roller 11 is shown in FIGS. 5 and 6. The first roller 11 is composed of a plurality of spur gears 11c and a plurality of spacers 11d. The gears 11c and the spacers 11d are coaxially mounted on a rotating shaft 15 to make up the shape of a roller. The gears 11c and the spacers 11d have the same thickness. Each of the gears 11c and the spacers 11d has a through-hole in the center, through which the rotating shaft 15 is inserted. The gears 11c, the spacers 11d, and the rotating shaft 15 each have a notch (not shown), and a key (not shown) is inserted into each notch to prevent the gears 11c and the spacers 11d from free-wheeling.

As illustrated in FIG. 6, the spacer 11d has a number of radial beams 11e of equal length. Assuming for descriptive purposes only that the diameter of an imaginary circle formed by connecting the tips of the beams 11e as an outside diameter of the spacer 11d, the spacer 11d has a smaller outside diameter than the gear 11c. The number of teeth of the gear 11c is an integer multiple of that of the beams 11e of the spacer 11d. In the present embodiment, the number of the beams 11e of the spacer 11d is 7, while the number of the teeth of the gear 11c is 21, an integer multiple of the former.

The gear 11c is placed on both sides of one spacer 11d to make a set of gears 16. A plurality of the set of gears 16 are arranged to make the first roller 11. Two gears 11c and one spacer 11d making each set of gears 16 are combined such that their teeth (the tip of the beam 11e of the spacer 11d will sometimes be referred to as a tooth) are in alignment parallel to the axial direction of the roller 11. Each set of gears 16 forms projections 17 and depressions 18 alternating in the rotating direction of the roller 11. The projections 17 of the set of gears 16 include those formed of three teeth aligned in a series in the axial direction (teeth of the two gears 11c and a tooth of the spacer 11d) designated 17a in FIG. 5 and those formed of two teeth discretely aligned in the axial direction (teeth of the gears 11c) designated 17b in FIG. 5. On the other hand, the depressions 18 are spaces between adjacent teeth of the gears 11c. The dimension of the projection 17 in the axial direction decides the dimension of the depression 6 of the composite sheet 1 in direction Y.

At least two sets of gears 16 are used to make the roller 11. The sets of gears 16 are mounted such that the positions of projections 17 of one set of gears 16 are different from those of the adjacent set(s) of gears 16 in the axial direction. In the present embodiment, two adjacent sets of gear 16 are offset by half the pitch of the projections and the depressions.

Each set of gears 16 has cavities 19 formed between a pair of the gears 11c at a given interval along the rotational direction of the roller 11. Each cavity 19 is formed by the pair of the gears 11c and the interposed spacer 11d. More specifically, each cavity 19 is defined by the opposing sides of the two gears 11c and two adjacent beams 11e of the spacer 11d. Accordingly, one set of gears 16 has as many cavities 19 as the number of the beams 11e of the spacer 11d. The cavities 19 are open to the outside in the above-identified depressions 18.

Each gear 11c has through-holes 20 arranged to encircle the central through-hole through which the rotating shaft 15 is inserted. The through-holes 20 are equal in diameter and distance from the center of the gear. They are circumferentially equally spaced. Each gear 11c has as many through-holes 20 as the number of beams 11e of the spacer 11d. The gears 11c and the spacer 11d are combined to make one set of gears 16 in such a configuration that each through-hole 20 may be positioned between two adjacent beams 11e of the spacer 11d. In other words, each through-hole 20 is positioned in a nearly V-shaped space defined by two adjacent beams 11e and the central portion 11f of the spacer 11d. While, in FIG. 5, the entire through-hole 20 is in the nearly V-shaped space, part of the hole may be out of the generally V-shaped space. Each nearly V-shaped space is one of independent sectors into which the gear 11c is sectioned so as to isolate the through-holes 20 from one another. The nearly V-shaped space connects to the depressions 18. Each set of gears 16 being so constructed, and a plurality of the sets of gear 16 being combined with their projections and depressions out of alignment in the axial direction, all the through-holes 20 connect to one another to form a plurality of interior suction paths 21 extending in the axial direction of the roller 11. Each suction path 21 connects to the cavity 19. The cavity 19 forms a part of the suction path 21.

As is understandable from above, the spacers 11d are used to form independent sectors in the roller 11. Each sector connects with the depressions 18 and the dedicated suction path 21. At least one end of every suction path 21 is connected to a suction source (not shown), such as a blower or a vacuum pump. On operating the suction source, air is drawn inward from the periphery of the roller 11, i.e., from the depressions 18 through the suction paths 21.

Beside forming the sectors, the spacers 11d are also used to support the gears 11c from both sides to provide the first roller 11 with strength. In the production of a composite sheet 1 with small sized projections 5, in particular, it is necessary to reduce the thickness of the gears 11c accordingly. This invites reduction of strength of the gears 11c. The beams 11e of the spacers 11d will work literally as beams, showing remarkable effects in preventing distortion of the gears 11c.

The roller 11 of the present embodiment is especially effective in forming a number of small projections at a small pitch. Even in using spur gears of small module, the cavities 19 may be designed to have a sufficient size for securing a sufficient area of the suction hole by increasing the thickness of the spacers 11d or reducing the number of the beams 11e. The structure of the roller 11 offers another advantage in that the pitch and size of the projections are freely adjustable by giving a simple alteration to the combination or the thicknesses of gears and spacers.

The structure of the second roller 12 is not particularly limited as long as it is shaped to engage with the first roller 11. It is preferred that the second roller 12 is composed of a plurality of gears similarly to the first roller 11 in terms of freedom of designing the structure of the roller 12. In constructing the second roller 12 by using a plurality of gears, the second roller 12 may be composed of the same gears as the gears 11c used in the first roller 11 either solely or in combination with disc-shaped spacers (hereinafter "disc spacers").

In the case when the second roller 12 is constructed by the same gears as the gears 11c used in the first roller 11 in combination with disc spacers, the gears and the spacers are arranged alternately. The axial position of the gears and the spacers should be adjusted so that the projections of the gears of the second roller 12 in meshing engagement with the first roller 11 may be located in the central region of the depressions 18 of the first roller 11. The diameter of the disc spacers is preferably equal to or smaller than the root diameter of the gears. The dimension of the projections of the second roller 12 may be increased by increasing the thickness of the gears used in the second roller 12 over the thickness of the gears 11c used in the first roller 11.

An engraved roller may be used as the second roller 12. A roller made up of gears and disc spacers as described is nevertheless preferred to an engraved roll for the following reason. Since the first roller 11 is composed of a plurality of gears 11c and a plurality of spacers 11d, it has accumulated thickness errors caused by machining errors in making the gears 11c and spacers 11d. Therefore, it is necessary that making an engraved roller as a second roller 12 involves adjustment in machining a whole work piece so as to achieve precision of meshing engagement with the first roller 11. On the other hand, in the case when the second roller is made up of gears and spacers, the error of the first roller 11 can be reflected by adjusting only the thickness of the disc spacers. As a result, the meshing positions can be adjusted with ease and by machining minimum parts.

Back to FIG. 4, the upper fibrous sheet 2 is fed at a higher speed than the peripheral speed of the first roller 11 and the second roller 12. By so feeding, the upper fibrous sheet 2 is prevented from deformation in the MD while being textured. The feeding speed of the upper fibrous sheet 2 is preferably 1.01 to 2.0 times higher than, more preferably 1.05 to 1.4 times higher than, the peripheral speed of the first and second rollers 11 and 12, while depending on the degree of texturing. The amount of feed is decided according to the height or depth of the texturing.

The upper fibrous sheet 2, while being fed at a higher speed than the peripheral speed of the rollers 11 and 12, is held by suction to the peripheral surface of the first roller 11, whereby it is prevented from shrinkage in the CD while texturing. It is only necessary that the upper fibrous sheet 2 is sucked to overlie the first roller 11. The upper fibrous sheet 2 does not have to be sucked to enter the depressions of the roller 11. Suction of the upper fibrous sheet 2 is achieved by drawing ambient air radially inward from periphery of the roller 11 through the suction paths 21 (see FIG. 5) formed inside the first roller 11 by suction means.

An arc along which the upper fibrous sheet 2 is held to the periphery of the first roller 11 forms an angle (i.e., the wrap angle) of preferably 2° to 10°, more preferably 5° to 10° to the center of the roller. If the wrap angle is extremely large, the upper fibrous sheet, being fed at a higher speed than the peripheral speed of the roller, may be slackened to form wrinkles on the periphery of the first roller 11 before it is fed into the bite between the first roller 11 and the second roller 12.

The upper fibrous sheet 2, while being sucked by the first roller 11, is introduced into the bite between the two rollers 11 and 12 and textured. The upper fibrous sheet 2 continues being sucked while traveling from the meshing nip of the first and second rollers 11 and 12 up to the meeting of the upper fibrous sheet 2 and the lower fibrous sheet 3. The upper fibrous sheet 2 having been textured between the first roller 11 and the second roller 12 in mesh is tightly held to the surface of the first roller 11 by the suction force exerted through the cavities 19 formed on the roller 11 and thus kept in the textured state. If the upper fibrous sheet 2 is not sucked, it will lift from the periphery of the first roller 11, resulting in a failure to obtain a composite sheet with a desired surface texture.

By this surface texturing, the projections 5 and the depressions 6 shown in FIG. 1 are formed. Since the upper fibrous sheet 2 is fed at a higher speed than the peripheral speed of the rollers 11 and 12, the texturing is performance without involving substantial extension of the sheet 2 in the MD. The seeming reduction in length in MD due to the texturing is supplemented by the higher speed feed of the sheet 2. Therefore, comparing the first walls 51 and the second walls 52 of the projections 5 formed by the texturing, the basis weight of the second walls 52 parallel to the direction perpendicular to the MD of the upper fibrous sheet 2 is not so different from that of the upper fibrous sheet before being textured for the following reason. In contrast, the basis weight of the first walls 51 parallel to the MD of the upper fibrous sheet 2 is much smaller than that of the upper fibrous sheet 2 before being textured. Although the sheet 2 must shrink in the CD (reduce in seeming width) as a result of texturing, the width shrinkage is restricted because, as previously stated, the upper fibrous sheet 2 is held to the periphery of the first roller 11 by suction until it is drawn into the engaged portion between the rollers 11 and 12. As a result, the sheet 2 is plastically deformed in its transverse direction instead of reducing its seeming width. The deformation greatly reduces the basis weight of the upper fibrous sheet 2 at the portions corresponding to the first walls 51 compared with the basis weight of the upper fibrous sheet before being textured. For the reason above, the basis weight of the first walls is smaller than that of the second walls.

Subsequently, as shown in FIG. 4, the upper fibrous sheet 2, while being tightly held to the periphery of the first roller 11, is superposed on the separately fed lower fibrous sheet 3, and the two sheets are introduced into the nip between the first roller 11 and an anvil roller 13, whereby the lower fibrous sheet 3 is thermally bonded to the upper fiber layer 2 at the parts corresponding to the top face of the projections on the first roller 11, i.e., the tooth faces of the gears. The anvil roller 13 or, where necessary, both the anvil roller 13 and the first roller 11 are previously heated to a prescribed temperature. Usually, heating only the anvil roller 13 is enough. As the case may be, heating both the anvil roller 13 and the first roller 11 can thermally damage or reduce the hand of the upper fibrous sheet 2. The upper fibrous sheet 2 and the lower fibrous sheet 3 may be bonded together by application of an adhesive or ultrasonication instead of the thermal bonding.

Figure 7:
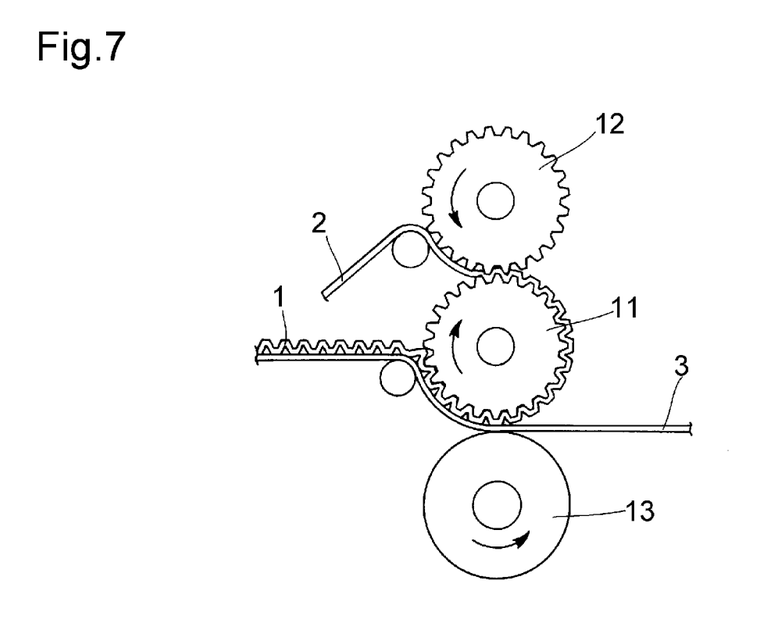
[FIG. 7] FIG. 7 schematically illustrates another process of producing the sheet of FIG. 1.
Figure 8:
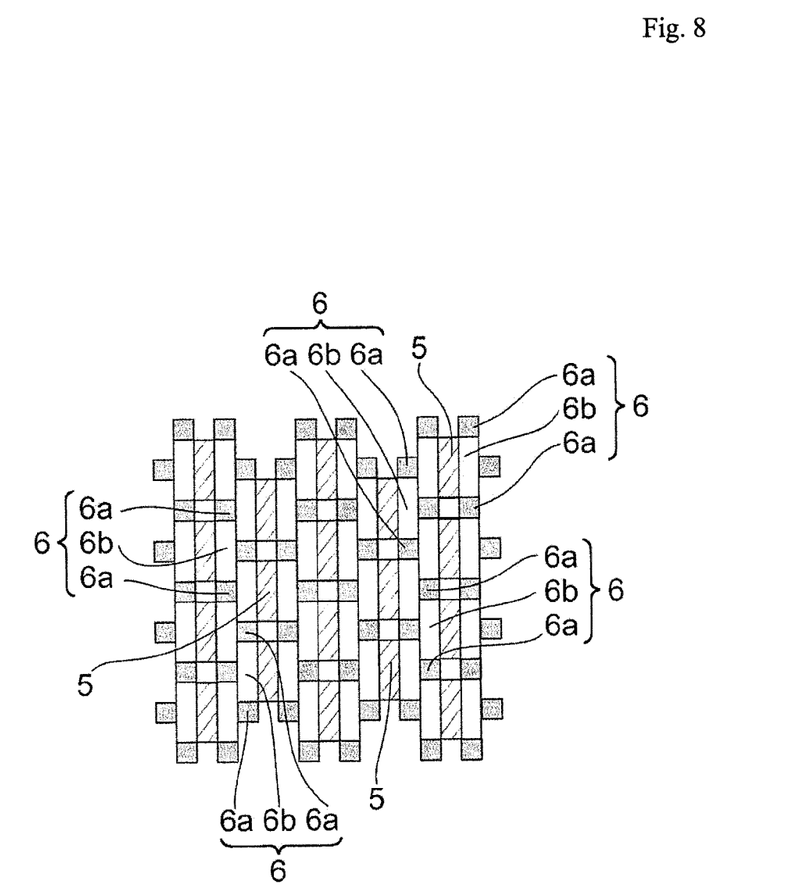
FIG. 8 is a plan of an alternative embodiment of the composite sheet according to the present invention, seen from the upper fibrous sheet side.

FIG. 7 illustrates another process of producing the composite sheet 1 using an apparatus different from that of FIG. 4. The difference between the apparatus shown in FIGS. 4 and 7 resides in the way of sucking the upper fibrous sheet 2 before being fed into the engaged portion between the rollers 11 and 12. While in FIG. 4 the upper fibrous sheet 2 is held to the periphery of the first roller 11, it is held in FIG. 7 to the periphery of the second roller 12. At the time when the upper fibrous sheet 2 is introduced into the engaged portion between the rollers 11 and 12, the suction by the second roller 12 is switched to the suction by the first roller 11 to carry out the texturing of the sheet 2. When in using the apparatus shown in FIG. 7 in place of the apparatus shown in FIG. 4, the composite sheet 1 is produced successfully as well.

As stated, the composite sheet 1 thus produced is suited for use as a topsheet of an absorbent article. An absorbent article generally includes a liquid permeable topsheet, a liquid impermeable backsheet, and a liquid retentive absorbent member interposed between the topsheet and the backsheet. The composite sheet is also useful in other applications, such as a backsheet of an absorbent article, an intermediate sheet between a topsheet and an absorbent member, a base of fastening tapes used in a taped disposable diaper, a landing sheet for receiving fastening tapes of a taped disposable diaper, a base of wings used in winged sanitary napkins, a base of a female portion of a hook & loop fastener, a cleaning sheet, and a wipe sheet.

While the present invention has been described with reference to the preferred embodiments thereof, the invention is not limited to the embodiments. For example, while in the embodiments described, the projections 5 and the depressions 6 are arranged in a staggered pattern, and every depression 6 is closed, being surrounded on all four sides by the projections 5, the individual depressions 6 may partly adjoin other depression or depressions.

While in the embodiments described the projections 5 and the depressions 6 are arranged in a staggered pattern, in which projections 5 and the depressions 6 alternating in a line extending in direction X (see FIG. 1) are out of alignment with those of adjacent lines by half the pitch, the amount of positional departure from alignment is not limited to half the pitch.

The projection 5 may be dome-shaped, in which case the first walls 51 are curved surfaces nearly parallel to the first direction of the composite sheet 1.

While in the application described above the first walls 51 are parallel with the longitudinal direction of an absorbent article, with the second walls parallel with the lateral direction of the absorbent article, the directional relation is not limited thereto. For example, a wide-width composite sheet 1 as produced is cut to length, and a cut sheet is turned 90° so that the second walls 52 may extend parallel to the longitudinal direction of an absorbent article, with the first walls 51 parallel to the lateral direction of the absorbent article.

The gears 11c and the spacers 11d, which have the same thickness in the foregoing embodiments, may have different thicknesses. The total thickness of each set of gear may vary from set to set.

The number of the teeth of the gear 11c, which is an integer multiple of the number of the beams 11e of the spacer 11d in the foregoing embodiments, does not always need to be an integer multiple.

While in the foregoing embodiments the spacer 11d has a smaller outside diameter than the gear 11c, the spacer 11d and the gear 11c may have the same outside diameter. In the latter case, the beams 11e take part in joining the two sheets at their tips so that the part of the individual depressions 6 of the resulting composite sheet 1 that corresponds to the non-bonded region 6b in the foregoing embodiments is a bonded region.

A plurality of the through-holes 20 made in the individual gears 11c do not need to have the same diameter as long as the uneven shape of the upper fibrous sheet 2 formed by texturing with the periphery of the first roller 11 is held by suction. The through-holes 20 do not need to be equally distant from the center of the gear 11c or circumferentially equally spaced apart.

The individual projections 5 of the composite sheet 1, while hollow in the foregoing embodiments, may be filled with fibers.

While in the foregoing embodiments the upper fibrous sheet 2 is held to the periphery of the first roller 11 or the second roller 12 before being introduced into the engaged portion between the first and second rollers 11 and 12, the upper fibrous sheet 2 may be fed into the engaged portion between the two rollers without being wrapped around either roll.

INDUSTRIAL APPLICABILITY

As described, the composite sheet of the present invention provides high cushioning properties and liquid permeability when used as, for example, a topsheet of an absorbent article.

The invention claimed is:

1. A composite sheet comprising a substantially flat lower fibrous sheet and an upper fibrous sheet bonded to the lower fibrous sheet, the upper fibrous sheet being three-dimensionally textured with a number of projections and a number of depression each of which is located between every adjacent two of the projections, the projections and the depressions alternating in a first direction of the composite sheet and in a second direction perpendicular to the first direction, the projections each having a pair of opposing first walls parallel to the first direction, a pair of opposing second walls parallel to the second direction, and a top plane connected to the upper edge of each first wall and the upper edge of each second wall, and the basis weight of each first wall being different from that of each second wall;

wherein the projections and the depressions are arranged in a staggered pattern in which the projections and the depressions alternating in a line extending in the first direction of the composite sheet are out of alignment with the projections and the depressions of the adjacent lines by half the pitch;

wherein the projections are hollow; and wherein individual depressions partly adjoin at least one other depression.

2. The composite sheet according to claim 1, wherein the first walls are parallel to the machine direction of the composite sheet, the second walls are parallel to the cross direction of the composite sheet, and the basis weight of the first walls is smaller than that of the second walls.

3. The composite sheet according to claim 2, wherein the first wall of the projection has a hole.

4. The composite sheet according to claim 1, which is used on a skin facing side of an absorbent article having an absorbent member with the upper fibrous sheet being adapted to face the skin of a wearer and the lower fibrous sheet facing the absorbent member.

5. An absorbent article comprising an absorbent member and the composite sheet according to claim 1, the upper fibrous sheet being adapted to face the skin of a wearer and the lower fibrous sheet facing the absorbent member.

6. The absorbent article according to claim 5, wherein the first walls are parallel to a longitudinal direction of the absorbent article, the second walls are parallel to a lateral direction of the absorbent article, and the basis weight of the first walls is smaller than that of the second walls.

7. The composite sheet according to claim 1, wherein the lower fibrous sheet is substantially inextensible.

8. The composite sheet according to claim 1, wherein the lower fibrous sheet has a basis weight of 5 to 50 g/m$^2$.

* * * * *